United States Patent
Dupuis et al.

(10) Patent No.: US 6,607,714 B1
(45) Date of Patent: *Aug. 19, 2003

(54) THICKENED COMPOSITION IN AQUEOUS MEDIUM AND PROCESS FOR THICKENING AQUEOUS MEDIUM

(75) Inventors: Christine Dupuis, Paris (FR); Jean Mondet, Aulnay sous Bois (FR); Roland Audebert, Saint Leu la Foret (FR); Christophe Tribet, Villiers sur Orge (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/710,300

(22) Filed: Sep. 17, 1996

(30) Foreign Application Priority Data

Sep. 18, 1995 (FR) ............................................ 95 10915

(51) Int. Cl.⁷ .................................................. A61K 7/06
(52) U.S. Cl. ................ 424/70.1; 424/70.14; 424/70.16; 424/70.19; 514/944
(58) Field of Search ........................... 424/70.14, 70.16, 424/4.7, 70.19; 514/944

(56) References Cited

U.S. PATENT DOCUMENTS

| | | | | |
|---|---|---|---|---|
| 4,839,166 A | * | 6/1989 | Grollier et al. | 424/71 |
| 5,008,105 A | * | 4/1991 | Grollier et al. | 424/70.14 |
| 5,425,939 A | * | 6/1995 | Guerrero et al. | 424/78.18 |
| 5,593,663 A | * | 1/1997 | Leng et al. | 424/65 |
| 5,609,862 A | * | 3/1997 | Chen et al. | 424/70.11 |
| 5,610,201 A | * | 3/1997 | Grollier et al. | 514/773 |
| 5,612,024 A | * | 3/1997 | Giede et al. | 424/70.11 |
| 5,679,329 A | * | 10/1997 | Dupuis et al. | 424/70.14 |

FOREIGN PATENT DOCUMENTS

| | | | |
|---|---|---|---|
| EP | 0770380 A1 | * | 5/1997 |
| FR | 2 598 611 | | 5/1987 |

OTHER PUBLICATIONS

"Principles of Polymer Science . . . Core" pp. 391, 238–240, 444–449, 1999.*

* cited by examiner

Primary Examiner—Thurman K. Page
Assistant Examiner—Lakshmi Channavajjala
(74) Attorney, Agent, or Firm—Finnegan, Henderson, Farabow, Garrett & Dunner, LLP

(57) ABSTRACT

A thickening system for aqueous medium, which can be used in the fields of cosmetics, dermatology or hygiene, comprising at least one amphiphilic polymer comprising at least one fatty chain and at least one hydrophilic unit, and at least one protein.

62 Claims, No Drawings

THICKENED COMPOSITION IN AQUEOUS MEDIUM AND PROCESS FOR THICKENING AQUEOUS MEDIUM

The present invention relates to a novel thickening system (agent), a composition in aqueous medium, comprising the novel thickening system, and the use of this novel thickening system in a composition in aqueous medium, in particular in the cosmetics field.

It is known to use, as an agent for thickening aqueous media, water-soluble or water-dispersible polymers, and in particular polymers which may be crosslinked. The thickening is then brought about by interlinking of the polymer chains, the polymers preferably having a long chain length and a high molecular weight.

It is also known to use, as a thickener for aqueous media, hydrophilic polymers containing hydrophobic groups, in the form of sequences, grafts and/or side groups distributed randomly. These polymers allow considerable thickening of the medium to be obtained even when they are used in small amounts. The thickening is generated by the formation of aggregates between the hydrophobic groups of the polymer, these aggregates constituting physical crosslinking points between the macromolecular chains.

However, it has been observed that the presence of hydrophilic polymers containing hydrophobic groups, even in small amounts, in compositions, especially cosmetic compositions, could adversely modify the cosmetic properties of the compositions, for example the feel or spreading properties.

It is also known to prepare hair compositions in gel form comprising polymers containing hydrophobic groups combined with surfactants; the gel is then formed by means of the formation of mixed micelles. However, it has been observed that the texture obtained often has a tendency to break, which makes the composition difficult to handle. Furthermore, the presence of an excess of surfactant could lead to certain drawbacks in the field of leave-in compositions.

Thus, there is a need for a thickening system which makes it possible to thicken, or even to gel, a composition comprising an aqueous medium, without having any influence on the cosmetic properties of the compositions.

The aim of the present invention is to propose such a thickening system which also allows adequate thickening to be obtained using a very small amount of thickening polymer.

One subject of the present invention is thus a composition in aqueous medium, comprising the combination of at least one amphiphilic polymer comprising at least one fatty chain and at least one hydrophilic unit, and of at least one protein including at least one hydrophobic group, wherein the protein is not the same as the amphiphilic polymer.

Another subject of the invention is the use, in particular in a composition in aqueous medium, of the combination of at least one protein including at least one hydrophobic group and of at least one amphiphilic polymer which contains at least one fatty chain and at least one hydrophilic unit, as a thickening agent, wherein, of course, the protein is different from the amphiphilic polymer.

Yet another subject of the invention is a process for thickening a composition in aqueous medium, in which at least one protein including at least one hydrophobic group and at least one amphiphilic polymer comprising at least one fatty chain and at least one hydrophilic unit are added to the composition, wherein the protein and the amphiphilic polymer are not the same.

Another subject of the invention is the use of at least one protein including at least one hydrophobic group in order to improve the thickening power of an amphiphilic polymer comprising at least one fatty chain and at least one hydrophilic unit.

It has thus been observed that such a combination makes it possible to obtain, in aqueous medium, a large increase in viscosity which can go as far as total gelation of the medium.

It is thus possible to achieve thickening, or even gelation, using smaller amounts of polymer, while at the same time retaining good cosmetic properties. It should be noted that the polymer alone, in the amounts at which it is used in the presence of protein, would not necessarily allow the medium to be thickened.

The protein/polymer interaction thus makes it very easy to control the degree of viscosity of the medium by simple mixing, in proportions which may be adjusted at will, two fluid solutions, namely an aqueous polymer solution and an aqueous protein solution.

One advantage of the invention lies in the fact that it is possible to obtain suitable thickening of the medium while at the same time providing certain skin care and/or skin treatment properties by appropriately selecting the protein.

Thus, it may be envisaged that the composition according to the present invention will:
 provide moisturizing effects, when the protein possesses these effects;
 provide a skin-regenerating effect, by supplying amino acids and proteins;
 provide a mild bactericidal effect, by using certain proteins such as lysozyme;
 provide anti-free-radical effects, by using proteins such as superoxide dismutases.

Furthermore, the polymer network may have a certain protective effect towards the protein, in particular with respect to denaturing agents such as temperature or acidity, this being particularly advantageous when the protein is an enzyme.

Moreover, the cosmetic composition obtained, and in particular one which is a hair composition, can spread easily, can have good handling properties, and can be eliminated well on rinsing.

Without being limited by this explanation, it may be considered that, within the context of the invention, the increase in viscosity of the medium may result from physical crosslinking between the polymer chains and the protein, the crosslinking being reversible and involving associations or interactions of hydrophobic type between, on the one hand, the hydrophobic groups of the polymer and, on the other hand, the hydrophobic sites of the protein.

These hydrophobic-type interactions can then lead to the gelation network.

Depending on the type of protein used, the hydrophobic sites of the protein may be found at the surface of the protein (globular or fibrous proteins, for example) or may be distributed throughout the protein chain (proteins of unordered structure, for example).

The polymers which can be used in the present invention are preferably amphiphilic polymers which contain at least one fatty chain, and thus a hydrophobic part, and at least one hydrophilic unit, and thus a hydrophilic part.

The hydrophobic part may be small in number relative to the rest of the polymer chain, and may be located laterally on the chain and distributed randomly (random copolymers) or distributed in the form of sequences or grafts (block copolymers or sequenced copolymers).

Water-soluble or water-dispersible polymers may be used.

Polymers which "swell" in water may also be used, in particular when the copolymer is partially crosslinked.

The polymers may be of any chemical nature; it is thus possible to select natural polymers, which may be modified; radical polymers, in particular vinyl or acrylic radical polymers; polycondensates; and mixtures thereof.

They can be preferably ionic or nonionic and are more preferably anionic or nonionic.

Among the polymers according to the invention of derived natural type, mention may be made in particular of:

cellulose ethers possessing hydrophobic substituents, which may be alkyl groups having more than 8 carbons.

Hydroxyethylcellulose substituted with hydrophobic groups may be mentioned. Among the commercial products used in the cosmetic field, mention may be made of Natrosol Plus Grade 330 sold by the company Aqualon.

quaternized cationic celluloses modified with groups containing at least one fatty chain, such as alkyl, arylalkyl or alkylaryl groups or mixtures thereof, in which the alkyl groups are preferably $C_8$–$C_{22}$;

quaternized alkylhydroxyethylcelluloses (cationic) such as the products Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda;

galactomannans possessing hydrophobic substituents, and in particular hydrophobic substituted guar gum. Some of these derivatives are described in particular in EP 281,360, the disclosure of which is specifically incorporated by reference herein.

pullulans modified with hydrophobic groups, in particular cholesterol groups.

gelatins modified with hydrophobic groups, and in particular modified with $C_6$ to $C_{18}$ alkyl groups.

mucopolysaccharides such as those made of glycosaminoglycan and hyaluronic acid.

Among the polycondensates which can be used in the context of the invention, mention may be made of associative polyurethanes which are nonionic sequenced copolymers including, in the chain, both hydrophilic sequences, usually of polyoxyethylene nature, and hydrophobic sequences, which may be aliphatic chain units alone and/or cycloaliphatic and/or aromatic chain units.

The resulting sequenced copolymers may preferably be of the triblock or multiblock type. The hydrophobic sequences may thus be at each end of the chain (triblock copolymers with a central polyoxyethylene sequence) or distributed simultaneously at the ends and in the chain (multisequenced copolymers). They may also be as grafts or as a star.

Mention may be made of the polymers described in the article by ZEYING MA, J. of Appl. Polymer Sci., Vol. 49, 1509–27 (1993), the disclosure of which is specifically incorporated by reference herein.

Among the commercial polymers, those which may be mentioned are SER-AD FX1100 and SER-AD FX1035 from Hüls.

Among the radical polymers according to the invention, those which may be mentioned are anionic acrylic polymers, in aqueous dispersion, generally referred to as HASE (hydrophobically modified alkali-soluble or swellable emulsion). These are acrylic copolymers which exist in the form of dispersions in water at acidic pH and which may be dissolved in water by complete neutralization of the anionic groups, that is to say above pH 8.

Some of these dispersions may preferably be partially crosslinked. This requires that the complete neutralization should not bring about the complete solubilization of the polymer particles, but should give rise to strong swelling of these particles, also leading to gelation of the medium.

These non-crosslinked or partially crosslinked copolymers are preferably terpolymers between a monomer bearing a carboxylic acid group (acrylic acid, methacrylic acid), a relatively water-insoluble monomer of the $C_1$ to $C_4$ acrylate or methacrylate type, such as ethyl acrylate, and a third monomer bearing a hydrophobic group, which may be attached laterally to the main chain.

This hydrophobic group may preferably be a linear or branched alkyl group and/or a cycloalkyl group and/or an aryl group. The hydrophobic group may preferably be attached to the main chain directly via an ether, ester, or amide, carbamate or urea bond. It may also preferably be attached to the main chain via a polyoxyethylenated sequence, which is itself fixed onto the chain by an ether, ester, amide, carbamate or urea bond. In the latter case, the side groups are preferably small grafts containing hydrophilic and hydrophobic sequences, and the properties of thickening aqueous media are of higher performance.

Such aqueous polymer dispersions are described in particular in Shay, Surface Coatings International, 1993 (11) 446–453, and in U.S. Pat. No. 4,421,902, U.S. Pat. No. 4,423,199 and U.S. Pat. No. 4,663,385 from Röhm & Haas and U.S. Pat. No. 4,384,096 from Dow Corning, the disclosures of which are specifically incorporated by reference herein.

Mention may also be made of the products Acusol 823 and Acrysol 25 or 22 from Röhm & Haas.

Among the radical polymers according to the invention, those which may also be mentioned are:

copolymers of acrylic acid or methacrylic acid with N-alkylacrylamides, and in particular copolymers of acrylic acid/N-alkylacrylamides having a $C_1$ to $C_{20}$ alkyl group, such as those described in the article Magny et al., Double Liaison, 451, pp. 52–55 (1993), the disclosure of which is specifically incorporated by reference herein. They may be obtained by direct copolymerization or by subsequent amidation of the acrylic acid chain.

Depending on the procedure used, the hydrophobic alkyl groups may be distributed randomly (amidation in homogeneous organic solution) or in sequenced form (amidation in aqueous medium where the amine initially forms aggregates of micelle type).

other anionic radical copolymers, such as copolymers between a monomer containing a carboxylic acid group, for example (meth)acrylic acid, and (meth) acrylate esters or amides bearing hydrophobic cycloaliphatic or aromatic groups, such as isobornyl or adamantyl groups.

Mention may also be made of copolymers with perfluoro monomers, in particular copolymers with perfluorohexyl (meth)acrylate; copolymers between a monomer bearing a sulphonic acid group (in particular 2-acrylamido-2-methyl-2-propanesulphonic acid, styrenesulphonic acid) and an alkyl (meth)acrylamide possessing at least 8 carbons.

nonionic acrylic copolymers, and in particular copolymers of acrylamide/N-alkylacrylamide type such as those described in Goodwin et al., Polymer in Aqueous Media=Performance Through Association, (J. E. Glassed) Adv. Chem. Ser. 223; Am. Chem. Soc., Washington D.C., p. 365 (1989), the disclosure of which is specifically incorporated by reference herein.

Mention may also be made of:

copolymers of maleic anhydride and of monomers including at least one fatty chain, such as N-octadecyl vinyl ether/maleic anhydride copolymers, for instance the product Gantrez AN-8194 sold by the company ISP;

copolymers of crotonic acid and of monomers including at least one fatty chain, such as vinyl acetateicrotonic acidivinyl neodecanoate terpolymers, for instance the product Resine 28-2930 sold by the company National Starch; or vinyl acetate/crotonic acid/allyl stearate terpolymers such as the products Mexomere PV and PB sold by the company Chimex;

(meth)acrylic acid polymers modified with groups including at least one fatty chain or copolymers of (meth) acrylic acid and of monomers including at least one fatty chain; these monomers are preferably chosen from hydrophobic monomers including a fatty chain, amphiphilic monomers including a hydrophobic part with a fatty chain and a hydrophilic part, or mixtures thereof. Mention may be made, by way of example, of:

crosslinked copolymers of acrylic acid/$C_{10}$–$C_{30}$ alkyl acrylate such as the products Pemulen TR 1, Pemulen TR 2, Carbopol 1382, Carbopol 1342 and Carbopol ETD 2020 sold by the company Goodrich;

(meth)acrylic acid/ethyl acrylate/alkyl acrylate copolymers such as the product Acusol 823 sold by the company Röhm & Haas and the product Imperon R sold by the company Hoechst;

acrylic acidivinyl isodecanoate crosslinked copolymers such as the product Stabylen 30 sold by the company 3V;

acrylic acid/vinylpyrrolidonellauryl methacrylate terpolymers such as the products Acrylidone LM, ACP-1184 and ACP-1194 sold by the company ISP;

acrylic acid/lauryl (meth)acrylate copolymers such as the products Coatex SX sold by the company Coatex;

(meth)acrylic acid/alkyl acrylate/polyethoxylated alkyl allyl ether terpolymers such as the products Rheovis-CR, -CR3, -CR2 and -CRX sold by the company Allied Colloids;

methacrylic acidlethyl acrylate/polyethoxylated stearyl allyl ether terpolymers such as the products Salcare-SC90 and -SC80 sold by the company Allied Colloids (stearyl polyethoxylated with 10 mol of ethylene oxide, referred to as steareth-10);

methacrylic acid/ethyl acrylate/polyoxyethylenated lauryl acrylate terpolymers such as the product Rheo 2000 sold by Coatex;

methacrylic acid/ethyl acrylate/polyoxyethylenated stearyl methacrylate terpolymers such as the products Acrysol 22, Acrysol 25 and DW-1206A sold by the company Röhm & Haas;

methacrylic acid/ethyl acrylate/polyoxyethylenated nonylphenyl acrylate copolymers such as the product Rheo 3000 sold by Coatex;

acrylic acid/polyoxyethylenated stearyl monoitaconate copolymers or acrylic acid/polyoxyethylenated cetyl monoitaconate copolymers such as the products 8069-72A and 8069-72B sold by National Starch;

methacrylic acid/butyl acrylate/hydrophobic monomer copolymers including a fatty chain, such as the product 8069-146A sold by National Starch;

acrylic acid/$C_{15}$ alkyl acrylate/polyethylene glycol acrylate (28 mol of ethylene oxide) terpolymers such as the product Dapral GE 202 sold by the company Akzo;

salts of a partial fatty acid ester of an acrylic acid dimethylethanolamine/polymer, such as the product Dapral GE 202 DMA sold by the company Akzo;

copolymers of acrylic acid/acrylate/amphiphilic monomer including a fatty chain with urethane groups, such as the product Additol VXW 1312 sold by Hoechst;

acrylic polymers modified with hydrophobic groups containing a fatty chain, such as the product CS-0406 sold by Röhm & Haas.

Depending on their nature, the polymers according to the invention may preferably be used in the form of aqueous solutions or in the form of aqueous dispersions.

It is possible to use, without discrimination, a film-forming polymer or a non-film-forming polymer, or even a mixture of film-forming and non-film-forming polymer.

In a preferred embodiment, the polymer according to the invention is thus a polymer in which the percentage and/or size of the hydrophobic groups are such that the hydrophobic groups are capable of combining, in aqueous medium, with other hydrophobic groups contained on the protein.

The proteins according to the invention are proteins including a hydrophobic group; the group may be naturally present in the protein, or may be added. The group may be quaternized or non-quaternized, and ionic or nonionic. In particular, mention may be made of proteins having, as a hydrophobic group, a fatty chain, for example an alkyl chain of 8–20 carbon atoms.

Mention may be made in particular, alone or as a mixture, of:

globular proteins: these are generally water-soluble proteins of reduced size, which in solution take the form of compact globules raning in size from 3 to 50 nanometers, among which mention may be made of:

albumins such as serum albumins (BSA), albumins extracted from egg white (ovalbumin) or albumins extracted from milk (lactalbumin).

certain enzymes such as lysozyme or proteases, in particular papain and trypsin.

globular proteins of plant origin, in particular wheat or soya proteins.

fibrous proteins: these are proteins which may become organized into long fibres, among which mention may be made of:

collagen and derivatives thereof such as tropocollagen and gelatin, proteins of muscle structure such as elastin, or which constitute the structure of membranes, such as spectrin, fibrous polymers of proteinic monomers having a low molecular mass, such as actin filament or fibrin.

proteins of unordered structure, with no tertiary structure, which in solution are in the form of random balls, among which mention may be made of caseins and mucins extracted from mucus (glycoproteins).

denatured proteins which can give aggregates resulting from the denaturation of a solution of lactalbumin, for example, or of various albumin solutions, or of casein solutions.

synthetic polypeptides having hydrophobic sequences, among which mention may be made of polypeptide homopolymers such as polylysine hydrochloride, and copolymers having polypeptide sequences or grafts.

Among the preferred proteins according to the invention, mention may be made of glycoproteins, which may be combined with mucopolysaccharides, or alternatively with papain, BSA or lysozyme which may be combined with radical polymers.

Mention may also be made of keratin or derivatives thereof, and hydrolysates of collagen, of proteins or of fibroin.

The proteins according to the invention may be in the form of aqueous solutions or optionally in the form of aqueous dispersions.

The combination according to the invention may in particular be used to thicken, or even to gel, aqueous media so as to obtain aqueous gels, for example. It may optionally be used within the context of the thickening of emulsions, in particular for surfactant-free emulsions, or for the thickening of aqueous dispersions.

Applications may thus be envisaged in particular in the fields of cosmetics, dermatology or hygiene, for the thickening in particular of cleansing gels or care gels for the skin or the hair, styling gels, antisun gels, make-up gels and buccodental gels.

An application may also be envisaged in the field of emulsions and in particular in oil-in-water emulsions, for example in care creams, cleansing creams or make-up creams for the skin or the hair, and antisun creams, or even hair creams.

The composition according to the invention preferably comprises less than 5% by weight of surfactant.

The amounts of protein and polymer to be added to an aqueous medium will be determined by those skilled in the art based on their general knowledge.

A representative composition is one in which the polymer is present in a concentration preferably ranging from 0.1 to 15% by weight, more preferably from 0.2 to 10%, by weight relative to the weight of the total polymer.

The amount of protein may preferably range from 0.005% to 0.2% by weight relative to the weight of the total polymer.

Preferably, the proteins are used in an amount such that a protein/polymer weight ratio ranging from 0.1:1 to 10:1 is obtained.

A thickened composition may thus be obtained, having a viscosity preferably ranging from 200 to 30,000 cp (mPa s), and comprising a very small amount of thickening agents, which may preferably range from about 0.8 to 3% by weight, relative to the total weight of the composition, for example.

Depending on the application envisaged, the composition may additionally comprise the usual constituents for this type of composition.

Mention may be made of any additive usually used in the field considered, such as pigments, fillers and/or pearlescent agents, antioxidants, fragrances, preserving agents, cosmetic or pharmaceutical active agents, moisturizers, vitamins, essential fatty acids, sunscreens, surfactants and self-tanning agents (for example DHA).

A person skilled in the art will of course take care to select this or these possible additional compounds, and/or their amount, such that the advantageous properties of the composition according to the invention are not, or are substantially not, adversely affected by the addition envisaged.

The invention is illustrated in greater detail in the examples which follow, which are not intended to be limiting. Examples 1 to 3 describe the preparation of three polymers used according to the invention, by amidation of a homopolymer of polyacrylic acid using a hydrophobic amine, according to the method of Wang, ACS Symposium Series, 467, pp. 218–231 (1991), the disclosure of which is specifically incorporated by reference herein.

Examples 4 and 5 describe the thickened media obtained by mixing a protein and a polymer.

EXAMPLE 1

Preparation of Polymer (A) Having a Degree of Substitution of 6%

The starting material used was a commercial polyacrylic acid of number average molecular weight 150,000 sold by Polysciences as an aqueous solution. This solution was purified by dialysis on a Spectrapor 4 membrane (cutoff threshold 12,000–14,000) and then dried by freeze-drying.

The amount of water contained was determined each time in the freeze-dried product.

12.31 g of purified, freeze-dried polyacrylic acid containing 15% by weight of water were introduced into a centrally-stirred reactor. 340 ml of N-methylpyrrolidone were added. Dissolution was carried out under hot conditions (50° C.) with stirring for 18 hours. When everything dissolved, the temperature was raised to 60° C.

2.3 g of octadecylamine dissolved in 40 ml of N-methylpyrrolidone were added dropwise in order to obtain a homogeneous mixture in the reactor.

2.04 g of dicyclohexylcarbodiimide dissolved in 40 ml of N-methylpyrrolidone were then added. The mixture was left to react for 24 hours with stirring, at 60° C.

The mixture was cooled on an ice-bath. A precipitate of dicyclohexylurea forms. The medium was filtered through a sinter funnel. The filtrate was neutralized with sodium methoxide dissolved in methanol, using 2.2 equivalents relative to the theoretical amount.

The mixture was stirred for two hours at room temperature. The neutralized polymer precipitated and was filtered off and then dried under reduced pressure.

The precipitate was dissolved in 100 ml of deionized water. A gel formed, which was purified of the N-methylpyrrolidone solvent retained by slow precipitation from 4 liters of methanol, with stirring. The precipitate was filtered off and then repurified with methanol, and was dried under reduced pressure.

The desired substituted polymer was obtained, in a yield of ≧90% relative to the theoretical amount.

The degree of octadecylacrylamide group substitution was determined by elemental analysis (N/C ratio) and by proton NMR in dilute solution (0.1 to 1%).

The analyses showed that the degree of substitution is 6% (molar % of hydrophobic groups introduced).

EXAMPLE 2

Preparation of Polymer (B) Having a Degree of Substitution of 4%.

The process was carried out according to the same procedure as in Example 1, adjusting the amounts of octadecylamine to obtain a degree of substitution of 4%, i.e. 1.2 equivalents of dicyclohexylcarbodiimide, and neutralization with 2.2 equivalents of sodium methoxide.

The yield was greater than 90%. The NMR analyses and the 5 elemental analyses gave respective degrees of substitution of 3.9% and 4.2%.

EXAMPLE 3

Preparation of Polymer (C) Having a Degree of Substitution of 8%.

The process was carried out with the same procedure as in Example 1, adapting the amount of octadecylamine to obtain a degree of substitution of 8 mol%. The yield is greater than 90%. The degree of substitution, determined by elemental analysis, was 8.2%.

EXAMPLE 4

Preparation of Polymer/protein Mixtures

The three polymers (A), (B) and (C) were combined with the 15 protein lysozyme, and the polymers (A) and (B) were combined with the proteins BSA and papain.

Lysozyme is a globular protein whose main physiological role is to catalyse the hydrolysis of cell walls. It is considered as a mild bactericide. Its molecular mass is 14,400 daltons. In solution, lysozyme is in the form of an ellipsoid about 4.5×3×3 nm in size. Its isoelectric point is 11. At pH 9, lysozyme is globally positive, with an average charge close to 5.7. 90% pure egg white lysozyme (Sigma Chemicals) was used.

Bovine serum albumin (BSA) is a globular protein whose main physiological function is to transport fatty acids of other hydrophobic compounds in plasma. Its molecular mass is 66,700 daltons. In solution, BSA has an ellipsoid shape 14×4×4 nm in size. Its isoelectric point is 4.9. At pH 9, BSA is globally negative, with an average charge of −27.6. A 95 to 99% pure BSA (Sigma Chemicals) was used.

Papain is a globular protein and a protease contained in the latex of carica papaya leaves. Its molecular mass is 23,400 daltons. In solution, it is virtually in the shape of a sphere with a diameter of about 4 nm. Its isoelectric point is 8.75. At pH 9, it may be considered as globally neutral.

A papain sold by Fluka was used.

Three stock solutions were prepared by mixing:

an aqueous protein solution (concentration of 1 to 10% by weight), an aqueous polymer solution totally neutralized with sodium hydroxide (concentration of 2 to 3% by weight), and an ammonium phosphate buffer solution with a phosphate ion concentration of 100 mM, the pH adjusted to 9 with aqueous ammonia.

Before use, the stock solutions of proteins and of phosphate buffer were filtered (Whatman filter, porosity 0.2 $\mu$m).

By mixing the stock solutions, various compositions according to the invention were prepared, comprising variable concentrations of polymer and of protein.

They all contained 20 mM of phosphate ions and 400 ppm of preserving agent (NaN$_3$). After mixing, the trapped bubbles were chased out by centrifugation and the compositions obtained were then stored at +4° C. for 24 hours before taking the measurements.

EXAMPLE 5

Study of the Thickened Compositions Obtained

The compositions obtained were characterized by determining the mechanical spectrum in a frequency range of between 0.1 and 100 rad/sec. For this, a Fluids Spectrometers rotary rheometer: RFS II from Rheometrix was used.

The measurements were taken at 25° C. on a cone/flat type geometry (angle of the cone 0.04 rad), 25 or 50 mm in diameter, with oscillation (in dynamic regime).

The deformation applied was equal to 10% and was within the linear domain of the response to the sinusoidal excitation.

For each frequency w, the modulus of elasticity G' and the modulus of loss G" of the medium was thus determined. The modulus G' characterizes the elastic nature of the medium (behavioural aspect of a solid) whereas the modulus G" characterizes its viscous fluid aspect (behavioural aspect of a fluid).

When a medium which was initially fluid or weakly thickened (absence of physical crosslinking) was used as starting material, G" is greater than G' throughout the sweep frequency range.

As the viscosity increased by physical crosslinking due to the polymer/protein association, G' and G" increased. However, G' increased more rapidly, with crosslinking, than G" and became greater than G" when the medium was gelled. The higher the value of G', the higher the crosslinking density in the network formed between the macromolecular chains of the polymer and the protein.

The critical threshold for formation of the gel could be determined by various physical methods, but beyond this threshold the modulus of elasticity G' was always higher than G". The comparison of G' and G", over the sweep frequency range, served here as a criterion for quantifying the extent of gelation.

For each polymer+protein mixture, the values of G' and G" were thus determined as a function of the frequency w.

The change in the slope tangent Tgδ(w)=G"(w)/G'(w) (according to Te Nijenhuis, Macromol 1989, 22, 411) was then studied for each mixture.

The curve of Tgδ could then be plotted as a function of the protein concentration for each value of frequency w.

The curves plotted at the various frequencies intersect at the same point, which was defined as corresponding to the gel point. It was thus possible to determine the protein concentration which gave rise to gelation of the aqueous medium.

Furthermore, when the protein concentration increased beyond the gel point, the medium became increasingly rigid; G' increased very greatly. If the percentage of protein was in large excess relative to the polymer, saturation of the sites of association borne by the polymer could be observed, and the macromolecules were then progressively disconnected from the network formed; G' decreased.

Beyond a certain protein excess, for certain mixtures, precipitation of the system was observed, in particular when all the polymer/protein charges were self-saturated. The protein concentration giving rise to the precipitation could thus be determined.

The results obtained are reported in the following tables. All the mixtures were at pH 9 and contain 20 mM of ammonium phosphate buffer and 400 ppm of NaN$_3$.

| Polymer (%) | Lysozyme (%) at the gel point | Lysozyme (%) at precipitation |
| --- | --- | --- |
| Polymer A | | |
| 0.38% | 0.01% | 0.8% |
| 0.53% | medium already gelled | 1.0% |
| 0.83% | medium already gelled | 1.5% |
| Polymer B | | |
| 0.58% | 0.040% | 0.9% |
| 0.83% | 0.035% | 1.1% |
| 0.92% | 0.045% | 1.1% |
| 1.25% | medium already gelled | 1.3% |

-continued

| | | |
|---|---|---|
| Polymer C | | |
| 0.59% | <0.01% | >1.0% |
| Polymer (%) | BSA (%) at the gel point | BSA (%) at precipitation |
| Polymer A | | |
| 0.83% | medium already gelled | — |
| Polymer B | | |
| 0.42% | 0.035% | — |
| 0.92% | 0.035% | — |
| Polymer (%) | Papain (%) at the gel point | Papain (%) at precipitation |
| Polymer A | | |
| 0.83% | medium already gelled | 2.5% |
| Polymer B | | |
| 0.92% | 0.13% | 3.5% |

It is thus observed that, in the majority of cases, the initial polymer solution was not gelled and the addition of small amounts of protein causes gelation. In certain cases, however, the polymer, alone, led to the production of an already-gelled medium.

Furthermore, it is also observed that, even if the starting polymer concentration was such that the polymer could already gel the medium, the addition of protein greatly increased the value of G', that is to say the strength of the gel.

Lastly, for all the polymers considered, at any polymer concentration, the addition of protein increased the modulus G' to a maximum value which corresponded to a maximum gelation force.

It was thus possible to control the force of the thickening or of the gelation by selecting a polymer/protein ratio for a given protein and a given polymer.

For a given polymer, it is also possible to select the protein and the protein/polymer ratio in order to obtain the desired effect.

EXAMPLE 6

Measurement of Viscosity

The viscosity at 25° C. of an aqueous composition comprising 1% or 2% by weight of active polymer material and 0.1% or 0.5% by weight of active protein material was measured.

The following results were obtained:

| Polymer | Protein | Viscosity |
|---|---|---|
| 1% Acrysol 22 | — | 1300 cps |
| | 0.1% Lifidrem KPUN | 1500 cps |
| | 0.1% Lipacide PK | 2260 cps |
| | 0.1% Lexeine QX3000 | 2620 cps |
| | 0.1% Hydrotriticum QS | 1500 cps |
| | 0.1% Promois silk LAQ | 3100 cps |

-continued

| Polymer | Protein | Viscosity |
|---|---|---|
| 2% Acrysol 44 | — | 520 cps |
| | 0.5% Lifidrem KPUN | 1200 cps |
| | 0.5% Croquat WKP | 2550 cps |
| | 0.5% Croquat K | 1200 cps |

The compounds used were as follows:

Acrysol 22 from Röhm & Haas: ethyl acrylate/methacrylic acid/oxyethylenated stearyl methacrylate terpolymer (55/35/10) as a 30 % by weight aqueous solution Lifidrem KPUN from Coletica: powdered, sterilized undecenoyl keratin from feathers Lipacid PK from Seppic: keratinous palmitoyl acid Lexeine QX3000 from Inolex: N-hydroxypropyl cocoyldimethylammonium collagen hydrolysate as a 30% aqueous solution Hydrotriticum QS from Croda: quaternized wheat protein (MW: 3000 daltons) hydrolysate, as a 30% aqueous solution Promois silk LAQ: quaternized fibroin hydrolysate, as a 30% aqueous-alcoholic solution Acrysol 44 From Rdhm & Haas: polyurethane with polyethoxylated alkyl end groups, as a 35% solution in a propylene glycol/water mixture (60/40)

CroquatWKP from Croda: quaternized wool keratin (MW: 1300 daltons) hydrolysate, as a 30% aqueous solution Croquat K from Croda: quaternized keratin (MW: 3000 daltons) hydrolysate, as a 33% aqueous solution.

It is thus observed that the addition of a protein, which was or was not quaternized, to a polymer made it possible to improve the thickening power of the polymer.

Furthermore, the composition obtained was of adequate viscosity, while at the same time comprising a small amount of thickener.

We claim:

1. A composition in an aqueous medium, comprising the combination of:

at least one amphiphilic polymer including at least one fatty chain and at least one hydrophilic unit, wherein said at least one amphiphilic polymer is selected from cellulose ethers possessing hydrophobic substituents, quatemized cationic celluloses modified with groups including at least one fatty chain, quatemized alkylhydroxyethyl celluloses, galactomannans possessing hydrophobic substituents, pullulans modified with hydrophobic groups, gelatins modified with hydrophobic groups, mucopolysaccharides, associative polyurethanes, anionic acrylic polymers containing hydrophobic groups, acrylic acid copolymers with N-alkylacrylamides, methacrylic acid copolymers with N-alkylacrylamides, copolymers between a monomer containing a carboxylic acid group and (meth)acrylate esters, copolymers between a monomer containing a carboxylic acid group and amides bearing cycloaliphatic or aromatic hydrophobic groups, copolymers with perfluoro monomers, copolymers of a monomer bearing a sulphonic acid group and an alkyl (meth)acrylamide possessing at least 8 carbons, non-ionic acrylic copolymers containing hydrophobic groups, copolymers of maleic anhydride and monomers containing at least one fatty chain, copolymers of crotonic acid and monomers containing at least one fatty chain, polymers of (meth)acrylic acid modified with groups containing at least one fatty chain, and copolymers of (meth)acrylic acid and monomers containing at least one fatty chain, at least one protein including at least one hydrophobic group, wherein said at least one protein is selected from globular proteins, fibrous proteins, proteins with an unordered structure, denatured proteins, and synthetic polypeptides having hydrophobic sequences, wherein said at least one amphiphilic polymer and said at least one protein together are present in concentration ranging from 0.8 to 3% by weight relative to the total weight of said composition, and wherein said at least one protein is present in a concentration ranging from 0.005% to 2% by weight, relative to the total weight of said composition, and a surfactant in an amount less than 5% by weight relative to the total weight of said compositions, wherein said composition has a viscosity ranging from 200 to 30,000 cp (mPa·s).

2. A composition according to claim 1, wherein said at least one amphiphilic polymer is selected from water-soluble amphiphilic polymers, water-dispersible amphiphilic polymers, and amphiphilic polymers swellable in water.

3. A composition according to claim 2, wherein said at least one amphiphilic polymer is selected from amphiphilic polymers swellable in water, and further wherein said amphiphilic polymer is partially crosslinked.

4. A composition according to claim 1, wherein said at least one amphiphilic polymer is in dispersion or in aqueous solution.

5. A composition according to claim 1, wherein said at least one amphiphilic polymer is selected from natural polymers, radical polymers, and polycondensates.

6. A composition according to claim 5, wherein said natural polymers are modified and wherein said radical polymers are selected from vinyl radical polymers and acrylic radical polymers.

7. A composition according to claim 1, wherein said at least one amphiphilic polymer is selected from anionic polymers and nonionic polymers.

8. A composition according to claim 1, wherein said non-ionic acrylic copolymers containing hydrophobic groups are of the acrylamide/N-alkylacrylamide type.

9. A composition according to claim 1, wherein said at least one protein containing at least one hydrophobic group possesses a fatty chain.

10. A composition according to claim 9, wherein said fatty chain is a fatty chain having from 8 to 20 carbon atoms.

11. A composition according to claim 1, wherein said globular proteins are selected from globular proteins of plant origin, albumins, and enzymes; said fibrous proteins are selected from collagen, collagen derivatives, proteins of muscle structure, proteins of membrane structure, and fibrous polymers of proteinic monomers having a low molecular mass; and said proteins with an unordered structure are selected from caseins and mucins.

12. A composition according to claim 1, wherein said at least one protein is selected from albumins, lysozyme, papain, glycoproteins, keratin, derivatives of keratin, collagen hydrolysates, protein hydrolysates, and fibroin hydrolysates.

13. A composition according to claim 1, wherein said at least one protein is in quaternized form.

14. A composition according to claim 1, wherein said at least one protein is in non-quaternized form.

15. A composition according to claim 1, wherein said at least one protein is in a form selected from an aqueous solution and a dispersion in water.

16. A composition according to claim 1, wherein said at least one amphiphilic polymer is present in an concentration ranging from 0.1 to 15% by weight, relative to the total weight of said composition.

17. A composition according to claim 16, wherein said at least one amphiphilic polymer is present in an concentration ranging from 0.2 to 10% by weight, relative to the total weight of said composition.

18. A composition according to claim 1, wherein the ratio of said at least one amphiphilic polymer to said at least one protein ranges from 0.1:1 to 10:1.

19. A composition according to claim 1, wherein said composition is in a form selected from an aqueous gel and an emulsion.

20. A composition according to claim 1, wherein said composition is in a form selected from an aqueous gel and an emulsion, and further wherein said composition is selected from a cosmetic composition, a dermatological composition and a hygienic composition.

21. A composition according to claim 20, wherein said composition is in the form selected from a cleansing or care gel for the skin, a cleansing or care gel for the hair, a styling gel, an antisun gel, a make-up gel, a buccodental gel, a care cream, a cleansing cream, a make-up cream for the skin, an antisun cream and a hair cream.

22. A thickening agent comprising the combination of:
   at least one amphiphilic polymer including at least one fatty chain and at least one hydrophilic unit, and
   at least one protein including at least one hydrophobic group.

23. A process for thickening a composition in aqueous medium comprising the step of:
   including the composition according to claim 1 in said composition in aqueous medium in an amount effective to achieve said thickening.

24. A composition according to claim 1, wherein said composition further comprises at least one adjuvant.

25. A composition according to claim 21, wherein said hair cream is a a make-up cream for the hair.

26. A composition in an aqueous medium, comprising the combination of:
   at least one amphiphilic polymer including at least one fatty chain and at least one hydrophilic unit, and
   at least one protein including at least one hydrophobic unit;
   wherein said at least one amphiphilic polymer is present in a I concentration ranging from 0.1 to 15% by weight relative to the total weight of said composition; and
   wherein said at least one protein is present in a concentration ranging from 0.005 to 2% by weight relative to the total weight of said composition.

27. A composition according to claim 1, wherein said anionic acrylic polymers containing hydrophobic groups are partially cross-linked.

28. A composition in an aqueous medium, comprising the combination of:
   at least one amphiphilic polymer including at least one fatty chain and at least one hydrophilic unit,
   at least one protein including at least one hydrophobic group,
   wherein said at least one amphiphilic polymer and said at least one protein together are present in a concentration ranging from 0.8 to 3% by weight relative to the total weight of said composition,
a surfactant in an amount less than 5% by weight relative to the total weight of said composition, and
wherein said composition has a viscosity greater than the aqueous medium.

29. The composition according to claim 19, wherein said at least one amphiphilic polymer is selected from water-soluble amphiphilic polymers, water-dispersible amphiphilic polymers, and amphiphilic polymers swellable in water.

30. The composition according to claim 29, wherein said at least one amphiphilic polymer is selected from amphilic polymers swellable in water, and further wherein said amphiphilic polymer is partially crosslinked.

31. The composition according to claim 28, wherein said at least one amphiphilic polymer is in dispersion or in aqueous solution.

32. The composition according to claim 28, wherein said at least one amphiphilic polymer is selected from natural polymers, radical polymers, and polycondensates.

33. The composition according to claim 32, wherein said natural polymers are modified and wherein said radical polymers are selected from vinyl radical polymers and acrylic radical polymers.

34. A composition in an aqueous medium, comprising the combination of:
at least one amphiphilic polymer including at least one fatty chain and at least one hydrophilic unit,
at least one protein including at least one hydrophobic group,
wherein said at least one protein is in non-quatemized form,
wherein said at least one protein is present in a concentration ranging from 0.005% to 2% by weight, relative to the total weight of said composition, and
wherein said at least one amphiphilic polymer and said at least one protein together are present in concentration ranging from 0.8 to 3% by weight relative to the total weight of said composition, and
a surfactant in an amount less than 5% by weight relative to the total weight of said compositions,
wherein said composition has a viscosity ranging from 200 to 30,000 cp (mPa·s).

35. A composition according to claim 34, wherein said at least one amphiphilic polymer is selected from water-soluble amphiphilic polymers, water-dispersible amphiphilic polymers, and amphiphilic polymers swellable in water.

36. A composition according to claim 35, wherein said at least one amphiphilic polymer is selected from amphiphilic polymers swellable in water, and further wherein said amphiphilic polymer is partially crosslinked.

37. A composition according to claim 34, wherein said at least one amphiphilic polymer is in dispersion or in aqueous solution.

38. A composition according to claim 34, wherein said at least one amphiphilic polymer is selected from natural polymers, radical polymers, and polycondensates.

39. A composition according to claim 38, wherein said natural polymers are modified and wherein said radical polymers are selected from vinyl radical polymers and acrylic radical polymers.

40. A composition according to claim 34, wherein said at least one amphiphilic polymer is selected from anionic polymers and nonionic polymers.

41. A composition according to claim 34, wherein said at least one amphiphilic polymer is selected from cellulose ethers possessing hydrophobic substituents; quatemized cationic celluloses modified with groups including at least one fatty chain; quaternized alkylhydroxyethylcelluloses; galactomannans possessing hydrophobic substituents; pullulans modified with hydrophobic groups; gelatins modified with hydrophobic groups; mucopolysaccharides; associative polyurethanes; anionic acrylic polymers containing hydrophobic groups; acrylic acid copolymers with N-alkylacrylamides; methacrylic acid copolymers with N-alkylacrylamides; copolymers between a monomer containing a carboxylic acid group and (meth)acrylate esters; copolymers between a monomer containing a carboxylic acid group and amides bearing cycloaliphatic or aromatic hydrophobic groups; copolymers with perfluoro monomers; copolymers of a monomer bearing a sulphonic acid group and an alkyl (meth)acrylamide possessing at least 8 carbons; nonionic acrylic copolymers containing hydrophobic groups; copolymers of maleic anhydride and monomers containing at least one fatty chain; copolymers of crotonic acid and monomers containing at least one fatty chain; polymers of (meth)acrylic acid modified with groups containing at least one fatty chain; and copolymers of (meth) acrylic acid and monomers containing at least one fatty chain.

42. A composition according to claim 41, wherein said nonionic acrylic copolymers containing hydrophobic groups are of the acrylamide/ N-alkylacrylamide type.

43. A composition according to claim 41, wherein said anionic acrylic polymers containing hydrophobic groups are partially cross-linked.

44. A composition according to claim 34, wherein said at least one protein containing at least one hydrophobic group possesses a fatty chain.

45. A composition according to claim 44, wherein said fatty chain is a fatty chain having from 8 to 20 carbon atoms.

46. A composition according to claim 34, wherein said at least one protein is selected from globular proteins; fibrous proteins; proteins with an unordered structure; denatured proteins; and synthetic polypeptides having hydrophobic sequences.

47. A composition according to claim 46, wherein said globular proteins are selected from globular proteins of plant origin, albumins, and enzymes; said fibrous proteins are selected from collagen, collagen derivatives, proteins of muscle structure, proteins of membrane structure, and fibrous polymers of proteinic monomers having a low molecular mass; and said proteins with an unordered structure are selected from caseins and mucins.

48. A composition according to claim 34, wherein said at least one protein is selected from albumins, lysozyme, papain, glycoproteins, keratin, derivatives of keratin, collagen hydrolysates, protein hydrolysates, and fibroin hydrolysates.

49. A composition according to claim 34, wherein said at least one protein is in a form selected from an aqueous solution and a dispersion in water.

50. A composition according to claim 34, wherein said at least one amrphiphilic polymer is present in a concentration ranging from 0.1% to 15% by weight, relative to the total weight of said composition.

51. A composition according to claim 50, wherein said at least one amphiphilic polymer is present in a concentration ranging from 0.2% to 10% by weight, relative to the total weight of said composition.

52. A composition according to claim 34, wherein the ratio of said at least one amphiphilic polymer to said at least one protein ranges from 0.1:1 to 10:1.

53. A composition according to claim 34, wherein said composition is in a form selected from an aqueous gel and an emulsion.

54. A composition according to claim 53, wherein said at least one amphiphilic polymer is selected from water-soluble amphiphilic polymers, water-dispersible amphiphilic polymers, and amphiphilic polymers swellable in water.

55. A composition according to claim 54, wherein said at least one amphiphilic polymers is selected from amphiphilic polymers swellable in water, and further wherein said amphiphilic polymer is partially crosslinked.

56. A composition according to claim 53, wherein said at least one amphiphilic polymer is in dispersion of in aqueous solution.

57. A composition according to claim 53, wherein said at least one amphiphilic polymer is selected from natural polymers, radical polymers, and polycondensates.

58. A composition according to claim 57, wherein said natural polymers are modified and wherein said radical polymers are selected from vinyl radical polymers and acrylic radical polymers.

59. A composition according to claim 34, wherein said composition is in a form selected from an aqueous gel and an emulsion, and further wherein said composition is selected from a cosmetic composition, a dermatological composition and a hygienic composition.

60. A composition according to claim 59, wherein said composition is in a form selected from a cleansing or care gel for the skin, a cleansing or care gel for the hair, a styling gel, an antisun gel, a make-up gel, a buccodental gel, a care cream, a cleansing cream, a make-up cream for the skin, an antisun cream, and a hair cream.

61. A composition according to claim 60, wherein said hair cream is a make-up cream for the hair.

62. A composition according to claim 34, wherein said composition further comprises at least one adjuvant.

\* \* \* \* \*

UNITED STATES PATENT AND TRADEMARK OFFICE
CERTIFICATE OF CORRECTION

PATENT NO.   : 6,607,714 B1
DATED        : August 19, 2003
INVENTOR(S)  : Christine Dupuis et al.

It is certified that error appears in the above-identified patent and that said Letters Patent is hereby corrected as shown below:

Column 12,
Lines 49 and 50, "quatemized" should read -- quaternized --.

Column 14,
Lines 7 and 11, "an concentration" should read -- a concentration --.
Line 52, "a I concentration" should read -- a concentration --.

Column 15,
Line 13, "amphilic" should read -- amphiphilic --.
Line 33, "non-quatemized" should read -- non-quaternized --.
Line 43, "compositions," should read -- composition, --.

Column 16,
Line 3, "quatemized" should read -- quaternized --.
Line 58, "amrphiphilic" should read -- amphiphilic --.

Column 17,
Line 10, "polymers" should read -- polymer --.
Line 14, "of" should read -- or --.

Signed and Sealed this

Second Day of December, 2003

JAMES E. ROGAN
*Director of the United States Patent and Trademark Office*